(12) United States Patent
Lerner et al.

(10) Patent No.: US 8,222,457 B2
(45) Date of Patent: Jul. 17, 2012

US008222457B2

(54) COORDINATION COMPOUNDS OF THE BORON GROUP

(75) Inventors: Wolfram Lerner, Oberursel (DE); Jens Röder, Goslar (DE); Hannes Vitze, Idstein (DE); Matthias Wagner, Niddatal (DE); Ulrich Wietelmann, Friedrichsdorf (DE)

(73) Assignee: Chemetall GmbH, Frankfurt am Main (DE)

( * ) Notice: Subject to any disclaimer, the term of this patent is extended or adjusted under 35 U.S.C. 154(b) by 553 days.

(21) Appl. No.: 12/514,591

(22) PCT Filed: Nov. 19, 2007

(86) PCT No.: PCT/EP2007/062499
§ 371 (c)(1),
(2), (4) Date: May 13, 2009

(87) PCT Pub. No.: WO2008/059065
PCT Pub. Date: May 22, 2008

(65) Prior Publication Data
US 2010/0029875 A1    Feb. 4, 2010

(30) Foreign Application Priority Data

Nov. 17, 2006 (DE) .......................... 10 2006 054 649

(51) Int. Cl.
| | |
|---|---|
| C07F 5/02 | (2006.01) |
| H01B 1/00 | (2006.01) |
| H01B 3/20 | (2006.01) |
| C09K 3/00 | (2006.01) |

(52) U.S. Cl. ...... 568/1; 252/500; 252/518.1; 252/519.14; 252/521.4; 252/182.12; 252/182.32; 252/509; 252/573; 252/574; 252/182.13; 429/188; 429/304; 429/321; 585/511; 585/525; 526/195; 556/402

(58) Field of Classification Search .................. 585/511, 585/525; 526/195; 556/402; 568/1; 252/500, 252/518.1, 519.14, 519.2, 519.34, 519.4, 252/182.12, 182.13, 182.32, 509, 510, 573, 252/574; 429/188, 304, 306, 321, 322
See application file for complete search history.

(56) References Cited

U.S. PATENT DOCUMENTS

| | | | |
|---|---|---|---|
| 4,060,674 A * | 11/1977 | Klemann et al. ............... | 429/337 |
| 4,148,756 A | 4/1979 | Langer | |
| 4,522,987 A | 6/1985 | Hogan et al. | |
| 4,542,081 A | 9/1985 | Armand et al. | |
| 4,543,399 A | 9/1985 | Jenkins et al. | |
| 4,564,647 A | 1/1986 | Hayashi et al. | |
| 4,588,790 A | 5/1986 | Jenkins et al. | |
| 5,032,652 A | 7/1991 | Chang | |
| 5,084,534 A | 1/1992 | Welborn et al. | |
| 5,405,922 A | 4/1995 | DeChellis et al. | |
| 6,210,863 B1 * | 4/2001 | Cunningham et al. ...... | 430/281.1 |
| 6,534,613 B2 * | 3/2003 | Ford et al. ...................... | 526/352 |
| 6,562,513 B1 * | 5/2003 | Takeuchi et al. ............... | 429/189 |
| 6,706,829 B2 | 3/2004 | Boussie et al. | |
| 6,713,577 B2 | 3/2004 | Boussie et al. | |
| 6,750,345 B2 | 6/2004 | Boussie et al. | |
| 6,777,510 B1 | 8/2004 | Philipp et al. | |
| 6,794,514 B2 | 9/2004 | Brümmer et al. | |
| 7,226,704 B2 | 6/2007 | Panitz et al. | |
| 2004/0157730 A1 | 8/2004 | Hlatky et al. | |
| 2004/0202957 A1 * | 10/2004 | Murota ....................... | 430/270.1 |
| 2004/0209124 A1 * | 10/2004 | Schmidt et al. ............... | 428/697 |
| 2005/0131171 A1 * | 6/2005 | Tohi et al. ..................... | 526/127 |

FOREIGN PATENT DOCUMENTS

| | | |
|---|---|---|
| DE | 10111410 | 7/2002 |
| DE | 10359604 | 7/2005 |
| EP | 00970976 | 12/1983 |
| WO | WO 88/02009 | 3/1988 |
| WO | WO 97/42227 A | 11/1997 |
| WO | WO 99/52631 A | 10/1999 |
| WO | WO 03/010171 | 2/2003 |

OTHER PUBLICATIONS

STIC, EIC structure search of May 15, 2012, see "12514591-392764-EICSEARCH.pdf".*
Böhm "Die Ethylenpolymerisation mit Ziegler-Katalysatoren 50 Jahre nach der Entdeckung", Angewandte Chemie 115 (2003) pp. 5162-5183.
Chen, et al. "Organo-Lewis Acids as Cocatalysts in Cationic Metal-locene Polymerization Catalysis. [..]", J. Am. Chem. Soc. 118 (1996) pp. 12541-12542.
Chen "Cocatalysts for Metal-catalyzed Olefin Polymerization: [..]", Chem. Rev. 100 (2000), pp. 1391-1434.
Feldman, et al. "Electrophilic Metal Precursors and -Diimine Ligand for Nickel(II)- [..]", Organometallics, 16 (1997), pp. 1514-1516.
Johnson, et al. "New Pd(II)- and Ni(II)-Based Catalysts for Polymerize ion of Ethylene and I α-Olefins", J. Am. Chem. Soc. 117 (1995) pp. 6414-6415.
Johnson, et al. "Copolymerization of Ethylene and Propylene with Functionalized Vinyl Monomers by Palladium(II) Catalysts", J. Am. Chem. Soc. 116 (1995) pp. 267-268.
Krossing, et al. "Nichtkoordinierende Anionen-Traum oder Wirklichket? [..]",Angewandte Chemie 116 (2004) pp. 2116-2142.
Rossi, et al. "Oligo(Ethylene Oxide)-Functionalized Siloxanes: [..]", Polymer Preprints, 46 (2005) pp. 723-724.
Fujiwara, et al., A new synthesis of nitrogen-containing heterocycles by means of organoaluminum reagents, Tetrahedron Letters (1984).
Gelman, at al., Palladium-Catalyzed Cross-Alkynylation of Aryl Bromides by Sodium Tetraalkynylaluminates, Journal of Organic Chemistry (XP002467074).
Pena, et al Multifold and sequential cross-coupling reactions with indium organometallics, Chem. Communications (XP002467075).

(Continued)

Primary Examiner — Peter F Godenschwager
Assistant Examiner — Jane L Stanley
(74) Attorney, Agent, or Firm — Fulbright & Jaworski L.L.P.

(57) ABSTRACT

A coordination compound of an element of the boron group, the production of the compound and methods of using the compound as an additive, stabilizer, catalyst, co-catalyst, activator for catalyst systems, conductivity improver, and electrolyte.

12 Claims, No Drawings

OTHER PUBLICATIONS

Schiefer, et al, Neutral and Ionic Aluminum, Gallium, and Indium Compounds carrying Two or three Terminal Ethynyl Groups, (2003) (XP002467076).

Rossi, et al. Organoboron compounds. XX. Trineopentylborane from the neopentyl Grignard reagent, Journ. of Organic Chem. (XP002467077).

Aktamkina, et al, Organometallic borates (Me3ECH2)4BM, wherein E= silicon, germanium, tin; M = lithium, tetramethylammonium. (XP002467078) (1980).

Madema, et al. Donor-stabilized trialkynylboranes, Crystal structure of CH5N-B(C. tplbond. CH)3 and electronic structure of B(C. tplbond. CH)3, (XP002467079 ) (1997).

* cited by examiner

COORDINATION COMPOUNDS OF THE BORON GROUP

This application is a §371 of PCT/EP2007/062499 filed Nov. 19, 2007, which claims priority from DE 10 2006 054 649.0 filed Nov. 17, 2006

The invention provides a coordination compound of an element of the boron group, the preparation of this compound and the use thereof as an additive, stabilizer, catalyst, cocatalyst, activator for catalyst systems, conductivity improver and electrolyte.

In particular, the invention provides a coordination compound of boron.

In general, boron compounds having one or more B—C atomic bonds are extremely labile compounds which ignite spontaneously in contact with air or oxygen. One example of these is triethylboron. In contact with air, this burns instantaneously with a green flame. Because of the hazardousness of these substances, such compounds cannot be employed generally.

Boron compounds with aryl radicals, such as, for example, $B(C_6H_5)_3$, are more stable in air. However, these are distinguished by a poor solubility in hydrocarbons. Alternative compounds contain fluorine-substituted groups, such as, for example, $B(C_6F_5)_3$ or salts such as $Li[B(C_6F_5)_4]$ and the corresponding ammonium salts of $[B(C_6F_5)_4]$.

Activation of the cationic catalytically active compound in the polymerization of olefins and α-olefins with certain Brønsted and Lewis acids is adequately known. Such systems are used in Ziegler and Ziegler-Natta polymerization of olefins, in particular in catalyst and precatalyst systems of metals of group 3-10, in catalyst and precatalyst systems based on complexes of metals of group 3-10 with delocalized π-bonded ligands or in complexes of metals of group 3-10 with delocalized 1-bonded ligands and other ligands with coordinating heteroatoms, such as oxygen, sulfur, phosphorus or nitrogen. This includes above all so-called single-site catalysts, that is to say metallocene, half-sandwich and constrained-geometry catalysts, and also specific "classic" coordination compounds of metals of group 3-10, such as "Brookhart" and other beyond-metallocene catalysts, in which metals of group 3-10 are coordinated by hetero atoms, such as oxygen, sulfur, phosphorus or nitrogen (WO-A-03/010171, U.S. Pat. No. 6,706,829, U.S. Pat. No. 6,713,577, U.S. Pat. No. 6,750,345, US-A-2004/0157730, U.S. Pat. No. 6,777,510, U.S. Pat. No. 6,794,514, J. Am. Chem. Soc. 1996, 118, 267-268; J. Am. Chem. Soc. 1995, 117, 6414-6415; Organometallics 1997, 16, 1514-1516; G. Fink, R. Mulhaupt, H. H. Brintzinger, Ziegler Catalysts, Recent Scientific Innovations and Technological Improvements, Springer Heidelberg, 1995; J. Scheirs, W. Kaminsky, Metallocene-Based Polyolefins, Preparations, Properties and Technology, volume 1 and 2, Wiley Series in Polymer Science, Wiley-VCH Weinheim, 2000). The disclosure from WO-A-03/010171, U.S. Pat. No. 6,706,829, U.S. Pat. No. 6,713,577, U.S. Pat. No. 6,750,345, US-A-2004/0157730, U.S. Pat. No. 6,777,510 and U.S. Pat. No. 6,794,514 is a constituent of the present description in its full scope. For activation of these systems, suitable Brønsted acids can transfer a proton to the precatalyst and form the cationic catalytically active compound in this way. Suitable Lewis acids can likewise form the cationic catalytically active compound, for example by abstraction of a negatively charged ligand. The cationic catalytically active compound is activated by means of a weakly coordinating anion and stabilized. For activation of the precatalyst, inter alia aluminium-alkyls or methylaluminoxane (MAO), usually in a toluene solution, are also employed. MAO is in general a compound of unclear composition which is obtained by hydrolysis of trimethylaluminium. During storage, the solution tends to polymerize and to form a gel, and the activity of the solution is also subject to severe variations. Lewis acids, such as, for example, $B(C_6F_5)_3$, or Brønsted acids, for example ammonium cations with, for example, $[B(C_6F_5)_4]$ anions, are likewise employed for activation of such systems (WO-A-03/010171; G. Fink, R. Mulhaupt, H. H. Brintzinger, Ziegler Catalysts, Recent Scientific Innovations and Technological Improvements, Springer Heidelberg, 1995; J. Scheirs, W. Kaminsky, Metallocene-Based Polyolefins, Preparations, Properties and Technology, volume 1 and 2, Wiley Series in Polymer Science, Wiley-VCH Weinheim, 2000; L. L. Böhm, Angew. Chem. 2003, 115, 5162-5183; E. Y.-X. Chen, T. J. Marks, Chem. Rev. 2000, 100, 1391-1434; T. J. Marks, J. Am. Chem. Soc. 1996, 118, 12451-12452; G. Erker, Dalton Trans. 2005, 1883-1890; I. Krossing, I. Raabe, Angew. Chemie. 2004, 116, 2116-2142). The fluorine substituents are a disadvantage in the use of fluorine-substituted compounds, such as $B(C_6F_5)_3$ and $[B(C_6F_5)_4]$ salts. These compounds are ecologically unacceptable. They are distinguished by a high persistence in the environment and a poor biodegradability, and on the other hand these substances and their degradation and combustion products are harmful to the earth's ozone layer.

$B(C_6F_5)_3$ is also used in organic synthesis as a catalyst and synthesis auxiliary substance. Above all, $B(C_6F_5)_3$ is suitable for synthesis of oligo(ethylene oxide)-functionalized siloxanes (N. A. A. Rossi, Z. Zhang, Q. Wang, K. Amine, R. West, Polymer Preprints 2005, 46, 723-724).

EP-B-0097076 discloses solid solutions for conduction of ions, in particular cations. These solid solutions comprise macromolecular materials and Li, Na or K salts of trivalent elements of the boron group in a four-coordination sphere. Ligands are aryl or alkylalkynyl groups R—C≡C with aprotic hydrocarbon radicals R. It is also reported that such compounds do not hydrolyse in water and have a high solubility in ethers, such as diethyl ether and tetrahydrofuran. According to the prior art to date, the use of such compounds is limited to solid electrolyte solutions. Furthermore, the substituted aryl and alkylalkynyl groups used for the synthesis can be synthesized only in a very involved manner. Such systems are too expensive for widespread commercial use and they have also so far not found acceptance on the market.

In the currently dominant battery design—lithium ion batteries with liquid electrolytes—practically exclusively lithium hexafluorophosphate ($LiPF_6$) is used as a conductive salt. This salt has the necessary prerequisites for use in high-energy cells, that is to say it is readily soluble in aprotic solvents, it leads to electrolytes with high conductivities and it has a high degree of electrochemical stability. Oxidative decomposition occurs only at potentials greater than 4.5 V. However, $LiPF_6$ has serious disadvantages which can be attributed chiefly to its lack of thermal stability (decomposition above approx. 130° C.). Furthermore, in contact with moisture caustic and toxic hydrogen fluoride is liberated, which on the one hand makes handling difficult and on the other hand attacks and damages-battery constituents, for example the cathode.

Against this background, there are intensive efforts to develop alternative conductive salts. As such, above all lithium salts with perfluorinated organic radicals have been tested. These are lithium trifluoromethanesulfonate ("Li triflate"), lithium imides (lithium bis(perfluoroalkyl-sulfonyl) imides) and lithium methides(lithium tris(perfluoroalkylsulfonyl)methides). All these salts require relatively involved preparation processes and are therefore relatively expensive, and have other disadvantages, such as corrosiveness towards aluminium or poor conductivity and the ecological disadvantages already described. Alternative conductive salts and electrolytes based on boron salts which are virtually insoluble in hydrocarbons are disclosed in DE-C-10111410 and DE-A-10359604 A, which are part of this description in their full scope.

Lithium organoborates have been investigated as a further class of compound for use as a conductive salt in rechargeable lithium batteries. However, because of the low stability to oxidation already described and safety objections in the handling of triorganoboranes, they are ruled out for commercial systems.

The object of the present invention is to overcome the disadvantages of the prior art.

In particular, the object of the present invention is to provide a compound which is readily soluble in hydrocarbons and aprotic solvents and stable towards oxygen, contains no fluorine substituents and has only a slight tendency towards-coordination on metal centres.

According to the invention, the object is surprisingly achieved by the features of the main claim. Preferred embodiments are to be found in the sub-claims.

In particular, the object is surprisingly achieved by a coordination compound of the boron group of the general formula I shown in the following:

Formula 1:

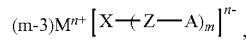

corresponding to $(m-3)M^{n+}[X(Z-A)_m]^{n-}$ in the linear written form,

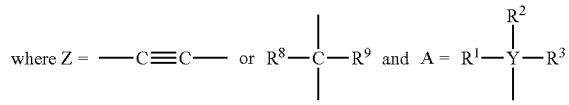

wherein:
$R^8$ and $R^9$ are chosen independently of one another from H, functionalized and/or non-functionalized branched and/or unbranched alkyl and/or cycloalkyl groups having 1 to 20 C atoms and/or functionalized and/or non-functionalized aryl and/or hetaryl groups having 1 to 12 C atoms;
$R^1$, $R^2$, $R^3$ are chosen independently of one another from functionalized and/or non-functionalized branched and/or unbranched alkyl and/or cycloalkyl groups having 1 to 50 C atoms and/or functionalized and/or non-functionalized aryl and/or hetaryl groups having 1 to 12 C atoms;
X is a trivalent element of the boron group in the three- or four-coordination sphere;
Y is a tetravalent element of the carbon group C, Si, Ge, Sn, Pb;
m=3 or m=4, wherein if m=3 then n=0 and if m=4 then n=1; and $M^+$=alkali metal, Li, Na, K, Rb, Cs, or $[(R^4R^5R^6R^7)N]^+$ or $H^+$ or $[(C_6H_5)_3C]^+$ or mixtures thereof; $R^4$, $R^5$, $R^6$, $R^7$ are chosen independently of one another from H, functionalized and/or non-functionalized branched and/or unbranched alkyl, alkenyl, alkynyl, cycloalkyl groups having 1 to 50 C atoms and/or aryl groups having 1 to 12 C atoms [sic] polymers.

Coordination compounds according to formula 1 according to the invention are trivalent elements of the boron group in three-coordination or salts of trivalent elements of the boron group in four-coordination with substituents other than aryl- or alkylaryl- or fluoroaryl- or fluoroalkylaryl-on the element of the boron group. The coordination compounds according to the invention are readily soluble in hydrocarbons, show a high stability towards oxygen and have a low tendency towards coordination on metal centres.

Examples of R, $R^1$, $R^2$, $R^3$ are: methyl, ethyl, ethenyl, ethynyl, n-propyl, iso-propyl, cyclopropyl, propen-3-yl, propyn-3-yl, n-butyl, cyclobutyl, 1-buten-4-yl, 1-butyn-4-yl, 2-buten-4-yl, crotyl, 2-butyn-4-yl, 2-butyl, iso-butyl, tert-butyl, n-pentyl, cyclopentyl, cyclopentadienyl, iso-pentyl, neopentyl, tert-pentyl, cyclo-hexyl, hexyl, n-heptyl, iso-heptyl, n-octyl, iso-octyl, thexyl, 2-ethyl-1-hexyl, 2,2,4-trimethylpentyl, nonyl, decyl, dodecyl, n-dodecyl, cyclopentyl, cyclopentenyl, cyclohexyl, cyclohexenyl, cycloheptyl, methylcyclohexyl, naphthyl, anthranyl, phenanthryl, o-tolyl, p-tolyl, m-tolyl, xylyl, ethylphenyl, mesityl, phenyl, benzyl, derivatives of substituted and unsubstituted aromatics, such as fluorene, indene and indane, or polymers. H, methyl, ethyl, iso-propyl, tert-butyl, thexyl, phenyl, benzyl and tolyl are preferred according to the invention.

Examples of $R^4$, $R^5$, $R^6$ and $R^7$ are: H, methyl, ethyl, ethenyl, ethynyl, n-propyl, iso-propyl, cyclopropyl, propen-3-yl, propyn-3-yl, n-butyl, cyclobutyl, 1-buten-4-yl, 1-butyn-4-yl, 2-buten-4-yl, crotyl, 2-butyn-4-yl, 2-butyl, iso-butyl, tert-butyl, n-pentyl, cyclopentyl, cyclopentadienyl, iso-pentyl, neopentyl, tert-pentyl, cyclo-hexyl, hexyl, n-heptyl, iso-heptyl, n-octyl, iso-octyl, thexyl, 2-ethyl-1-hexyl, 2,2,4-trimethylpentyl, nonyl, decyl, dodecyl, n-dodecyl, cyclopentyl, cyclopentenyl, cyclohexyl, cyclohexenyl, cycloheptyl, methylcyclohexyl, naphthyl, anthranyl, phenanthryl, o-tolyl, p-tolyl, m-tolyl, xylyl, ethylphenyl, mesityl, phenyl, benzyl and derivatives of substituted and unsubstituted aromatics, such as fluorene, indene and indane. Ammonium salts trisubstituted by hydrocarbons, such as trimethylammonium, triethylammonium, tripropylammonium, triisopropylammonium, tri(n-butyl)ammonium, N,N-dimethylphenylammonium, N,N-dimethylbenzylammonium, N,N-diethylphenylammonium, N,N-diethylbenzylammonium, N,N-dimethyl(2,4,6-trimethylphenyl)-ammonium, N,N-dimethyl(2,4,6-triethylphenyl)ammonium, N,N-dimethyl(2,4,6-trimethylbenzyl)ammonium, N,N-dimethyl(2,4,6-triethylbenzyl)ammonium, N,N-di(tetradecyl)phenylammonium, N,N-di(tetradecyl)(2,4,6-trimethylphenyl)ammonium, N,N-di(octadecyl)phenylammonium, N,N-di(octadecyl)(2,4,6-trimethylphenyl)ammonium, methyldicyclohexylammonium, N,N-dimethylphenylammonium, tetra(n-butyl)ammonium and triphenylammonium, are preferred according to the invention. N,N-Dimethylphenylammonium, methylbis(octadecyl)ammonium, dimethyloctadecylammonium, methylbis(tetradecyl)ammonium, N,N-bis(octadecyl)phenylammonium and N,N-bis(octadecyl)(3,5-dimethylphenyl)ammonium are particularly preferred according to the invention. Mixtures of variously substituted ammonium ions are furthermore preferred according to the invention. Examples of these are the commercially obtainable amines which contain mixtures of two $C_{14}$, $C_{16}$ or $C_{18}$ alkyl groups and a methyl group. Such amines are obtainable from Chemtura under the trade name Kemamine™ T9701 and from Akzo-Nobel under the trade name Armeen™ M2HT.

The trityl cation $[(C_6H_5)_3C]^+$, the triphenylcarbonium ion, is likewise preferred according to the invention.

Examples of X are: boron, aluminium, gallium, indium and thallium. Boron and aluminium are particularly preferred according to the invention.

Coordination compounds according to formula 1 which are particularly preferred according to the invention are: tris(trimethylsilylmethyl)borane, tris(triisopropylsilylmethyl)borane, tris(tritert-butylsilylmethyl)borane, tris(trimethylsilylethynyl)borane, tris(triisopropylsilylethynyl)borane, tris(triisopropylethynyl)aluminium, tris(tritert-butylsilylethynyl)borane, tripropynylborane, triisopropynylborane, tributynylborane and the lithium, N,N-dimethylphenylammonium, tetra(alkyl)ammonium, tetra(n-butyl)ammonium salts and triphenylcarbonium salts of the anions tetrakis(trimethylsilylmethyl)borate, tetra-kis(triisopropylsilylmethyl)borate, tetrakis(tritert-butylsilylmethyl)borate, tetrakis(tri-methylsilylethynyl)borate, tetrakis-(triisopropylsilylethynyl)borate, tetrakis(triisopropylsilylethynyl)aluminate, tetrakis(tritert-butylsilylethynyl)borate, tetrapropynylborate, tetraisopropynylborate, tetrabutynylborate and dipropynyldibutynylborate.

The coordination compound according to the invention is distinguished by a high solubility in hydrocarbons.

The coordination compound according to the invention is distinguished by a low tendency towards coordination on metal centres.

The coordination compound according to the invention is distinguished by a high stability to oxygen.

The coordination compound according to the invention is distinguished by a high thermal stability.

The coordination compound according to the invention contains no fluorine atoms and is therefore more environment-friendly compared with the prior art.

The conductivity of the coordination compound according to the invention is just as good or better compared with commercially available conductive salts.

The invention also provides the preparation of the coordination compound according to the invention.

The invention also provides the use of the coordination compound according to the invention as a co-catalyst and activator for catalyst systems, in particular a co-catalyst and activator for catalyst systems in the polymerization of olefins.

Monomers which can be polymerized with the aid of catalysts in which a coordination compound according to the invention or several coordination compounds according to the invention are used include ethylenically unsaturated monomers, acetylenes, conjugated and/or non-conjugated dienes and polyenes. The monomers include olefins, for example $\alpha$-olefins having 2 to 20,000, preferably 2 to 20 and particularly preferably 2 to 8 C atoms or combinations of two and/or more such $\alpha$-olefins. Examples of such $\alpha$-olefins are ethylene, propene, 1-butene, 1,4-butadiene, 1-pentene, 4-methylpent-1-ene, isoprene, 1-hexene, 1-heptene, 1-octene, 1-nonene, 1-decene, 1-undecene, 1-dodecene, tridecene, 1-tetradecene, 1-pentadecene or combinations of these, as well as long-chain oligomeric or polymeric reaction products with vinyl end groups and $\alpha$-olefins having 10 to 30 C atoms, which are added to the reaction mixture in order to obtain long branchings within the polymer. Preferred $\alpha$-olefins for this are ethylene, propene, 1-butene, 1,4-butadiene, 1-pentene, 4-methylpent-1-ene, isoprene, 1-hexene, 1-heptene, 1-octene and combinations of ethylene and/or propenes with another $\alpha$-olefin. Other preferred monomers include styrene, halogen- or alkyl-substituted styrene derivatives, vinylbenzocyclobutene, 1,4-butadiene, 1,4-hexadiene, dicyclopentadienes, ethylidenenorbornenes and 1,7-octadiene. Mixtures of the monomers mentioned can likewise be employed.

The invention also provides the use of the coordination compound according to the invention as a co-catalyst and activator for catalyst systems in the polymerization of olefins, in particular as a co-catalyst and activator for Ziegler and/or Ziegler-Natta and/or single-site and/or metallocene and/or half-sandwich and/or constrained-geometry and/or beyond-metallocene catalysts.

Suitable catalysts for the reaction with the coordination compound according to the invention are all compounds or complexes of metals of group 3-10 of the periodic table which can be activated and have the ability to polymerize unsaturated compounds, for example olefins, $\alpha$-olefins, ethylene, propene and compounds with ethylene groups.

Particularly suitable catalysts for the reaction with the coordination compound according to the invention are all compounds or complexes and mixtures of compounds or complexes of scandium in oxidation levels +2 and/or +3, titanium and/or zirconium and/or hafnium in oxidation levels +2, +3 and/or +4, and/or manganese and/or iron in oxidation levels −2, −1, 0, +2, +3, +4, +5, +6 and/or +7 and/or nickel and/or palladium and/or platinum in oxidation levels −2, −1, 0, +2, +3 and/or +4 and/or lanthanum and/or neodymium in oxidation levels +1, +2 and/or +3 which can be activated and have the ability to polymerize unsaturated compounds, olefins, $\alpha$-olefins, ethylene, propene and compounds with ethylene groups.

The invention also provides the use of the coordination compound according to the invention as a co-catalyst and activator for catalyst systems in the polymerization of olefins in high and/or low pressure and/or in solution and/or in suspension and/or in gas-phase polymerization processes, both in discontinuous and in continuous processes. The disclosure from WO-A-88/02009, U.S. Pat. No. 5,084,534, U.S. Pat. No. 5,405,922, U.S. Pat. No. 4,588,790, U.S. Pat. No. 5,032,652, U.S. Pat. No. 4,543,399, U.S. Pat. No. 4,564,647 and U.S. Pat. No. 4,522,987 is a constituent of the present description in its full scope.

Suitable polymerization processes include solution processes, preferably continuous solution processes in the presence of an aliphatic and/or alicyclic and/or aromatic solvent or mixtures thereof. The term aliphatic and alicyclic solvent includes straight-chain, branched and cyclic C2 to C20-alkanes, cyclohexane, cycloheptane, methylcyclohexane and methylcycloheptane. Aromatic solvents, such as toluene, xylenes (all isomers), cumene or ethylbenzene, are also suitable. Monomers, such as ethylene, propene, butadiene, isoprene, cyclopentene, 1-hexene, 3-methyl-1-pentene, 4-methyl-1-pentene, 1,4-hexadiene, 1-octene, 1-decene, styrene, divinylbenzene, allylbenzene and vinyltoluene, are likewise suitable as solvents. All the isomers of the compounds and mixtures of monomers are included here. The activation of the catalyst with the coordination compound according to the invention can also be carried out in the solvents listed.

The invention also provides the use of the coordination compound according to the invention as a co-catalyst and activator for catalyst systems in the polymerization of olefins in heterogeneous and/or homogeneous processes.

The invention also provides the supporting of the coordination compound according to the invention on a solid support material. The supporting can be carried out by means of impregnation, deposition on the surface, physisorption or by means of a chemical reaction on the surface, in order to form a heterogeneous catalyst component which can be used for the polymerization of the monomers mentioned.

The molar ratio of the coordination compound according to the invention to the catalyst material is 1,000:1 to 1:1, preferably 200:1 to 1:1, particularly preferably 20:1 to 1:1.

The addition of the coordination compound according to the invention to the catalyst material can be carried out at any desired point in time of the polymerization reaction. The addition can be carried out before the start of the polymerization reaction and/or during the polymerization reaction, or can also be carried out continuously or discontinuously from before the start of the polymerization reaction up to any desired point in time during the polymerization reaction. The formation of the catalytically active component comprising the coordination compound according to the invention and the catalyst can be carried out outside and/or within the reactor in which the polymerization is carried out.

The catalysts prepared with participation of the coordination compounds according to the invention can be used with at least one or more further catalysts together in the same reactor or in separate but connected reactors, in order to prepare polymer mixtures with the desired properties.

The coordination compound according to the invention can be employed together with a reagent for controlling the molecular weight. These are, in addition to hydrogen and trialkylaluminium compounds, also other substances for polymer chain transfer.

The coordination compound according to the invention is preferably employed together with an oligomeric or polymeric aluminoxane compound and/or a tri(hydrocarbon)aluminium and/or a di(hydrocarbon)aluminium chloride and/or a hydrocarbonaluminium dichloride compound. Such aluminium compounds are usually added as "scavengers" in order to remove impurities.

The aluminium compounds preferred for this purpose include C1 to C20 trialkylaluminium compounds, in particular those with methyl, ethyl, propyl, isopropyl, n-butyl, isobutyl, pentyl, neopentyl or isopentyl groups, and diethylaluminium chloride, dialkyl(aryloxy)aluminium compounds having 1 to 6 C atoms in the alkyl groups and 6 to 18 C atoms in the aryl group, preferably 3,5-di(t-butyl)-4-methylphenoxy)diisobutylaluminium), methylaluminoxanes, modified methaluminoxanes, preferably isobutyl-modified methaluminoxanes, and tri(ethylaluminium)-, tris(pentafluorophenyl)borane- or tris(pentafluorophenyl)aluminium-modified methaluminoxanes, or supported derivatives of these.

The coordination compounds according to the invention are suitable for the preparation of high-density polyethylene (HDPE), medium-density polyethylene (MDPE), linear low-density polyethylene (LLDPE) and polypropylene (PP).

The invention also provides bottles, films, foils, fibre substances, shaped articles, shoe soles, foams, polymers having a vitreous appearance, automobile tyres, rubbers, lacquers, powder coatings, pipelines, drinking water pipes, waste water pipes, profiles, window profiles, foodstuffs packaging, blister packs and industrial plastics produced from polymers using the coordination compound according to the invention.

The invention also provides the use of the coordination compound according to the invention as a catalyst and/or synthesis auxiliary substance in organic synthesis.

The invention also provides the use of the coordination compound according to the invention in organic synthesis as a catalyst and/or synthesis auxiliary substance for the synthesis of oligo(ethylene oxide)-functionalized siloxanes.

The invention also provides the use of the coordination compound according to the invention as an electrolyte and conductive salt.

The invention also provides the use of the coordination compound according to the invention for the preparation of electrolytes and conductive salts.

The invention also provides the use of the coordination compounds according to the invention as an electrolyte in galvanic cells.

The invention also provides the use of the coordination compound according to the invention for the preparation of electrolytes for galvanic cells.

The invention also provides the use of the coordination compound according to the invention as an electrolyte in lithium batteries, preferably in lithium ion batteries.

The invention also provides the use of the coordination compounds according to the invention as an electrolyte in electrolytic double-layer capacitors.

The coordination compound according to the invention can be employed as an electrolyte in all the usual solvents. Alicyclic ethers, aliphatic and aliphatic difunctional ethers, esters carbonates, nitriles, amines, acid amides, ionic liquids, hydrocarbons, halogenated hydrocarbons, heterocyclic compounds and heteroaromatics are preferred. Diethyl ether, tetrahydrofuran, tetrahydro-2-methylfuran, tetrahydro-3-methylfuran, tetrahydro-2,5-dimethylfuran, tetrahydro-3,4-dimethylfuran, tetrahydropyran, cyclopentyl methyl ether, dimethoxyethane, diethoxymethane, diethoxyethane, polyethylene glycols, methyl formate, ethyl formate, propyl formate, methyl acetate, ethyl acetate, butyl acetate, methoxyethyl acetate, ethoxyethyl acetate, 2-(2-ethoxyethoxy)ethyl acetate, (2-methoxyethyl)methyl carbonate, ethylene carbonate, propylene carbonate, butylene carbonate, vinylene carbonate, dimethyl carbonate, diethyl carbonate, dipropyl carbonate, ethyl methyl carbonate, methyl propyl carbonate, butyl methyl carbonate, ethyl propyl carbonate, butyl ethyl carbonate, γ-butyrolactone, γ-valerolactone, dimethylformamide, dimethylacetamide, dimethylsulfoxide, triethylamine, piperidine, pyridine, acetonitrile, propionitrile, glutarodinitrile, adiponitrile, methoxypropionitrile, pentane, hexane, cyclohexane, heptane, methylcyclohexane, octane, benzene, toluene, xylenes (all isomers), ethylbenzene, cumene, methylene chloride, chloroform and 1,2-dichloroethane are particularly preferred. The pure solvents or mixtures thereof are preferred.

Further additives can be added to the electrolyte solutions prepared using the coordination compounds according to the invention.

The following examples are intended to explain the invention in more detail, without limiting it thereto.

EXAMPLE 1

General Preparation of the Compound According to Formula 1 According to the Invention All the reactions are carried out under an inert gas atmosphere, for example $N_2$, Ar or He.

The correspondingly substituted and metallized compound M-Z-A is reacted with a compound of an element of the boron group (boron group element compound), preferably with a boron compound, in a suitable solvent. The ratio of the metallized compound to the boron group element compound is preferably 3 to 6 equivalents of the metallized compound to one equivalent of the suitable boron group element compound. Suitable solvents for carrying out the reaction are, for example, hydrocarbons or ethers. Hexane or heptane or toluene or xylene or diethyl ether or dibutyl ether or methyl tert-butyl ether or tetrahydrofuran or tetrahydro-2-methylfuran or mixtures of at least two of these solvents are preferred. Boron- or aluminium-halogen compounds, for example $BF_3$, $BCl_3$ or $AlCl_3$, or boric acid esters are preferred for the preparation of suitable boron group element compounds. The boron-halogen compound can be employed in the pure form or as a complex with diethyl ether or tetrahydrofuran or tetrahydro-2-methylfuran. Boric acid esters, such as trimethyl borate, triethyl borate and triisopropyl borate, for example, are furthermore suitable. $BF_3$, $BCl_3$ and $B(OMe)_3$ are particularly preferred according to the invention. The reaction temperature is from −100° C. to 200° C. A temperature range of from −78° C. up to the boiling point of the solvent used is preferred, particularly preferably from −20° C. up to the boiling point of the solvent used. After the reaction, the compound according to formula 1 according to the invention can be isolated. The cation M+ caused by the reaction can be exchanged for other cations M+, for example by means of ion exchangers or re-formation of salts or recrystallization. Suitable solvents for exchanging the cation are hydrocarbons or ethers or aprotic organic solvents or protic organic solvents or alcohols or esters or water or mixtures of at least two of these solvents. Hexane or heptane or toluene or diethyl ether or dibutyl ether or methyl tert-butyl ether or tetrahydrofuran or tetrahydro-2-methylfuran or methanol or ethanol or iso-propanol or acetonitrile or dimethylsulfoxide or dimethylacetamide or poly(propylene) oxide or poly(ethylene)oxide or ethyl acetate or diethoxymethane or dimethoxyethane or propylene carbonate or water or mixtures of at least two of these solvents are preferred.

EXAMPLE 2

Preparation of Lithium tetrakis(trimethylsilylethynyl)borate

Trimethylsilylethyne is reacted with n-butyllithium in tetrahydrofuran. The trimethylsilylethynyllithium obtained is reacted with $BCl_3$. The LiCl is filtered off and the solvent is removed in vacuo.

EXAMPLE 3

Preparation of tris(trimethylsilylethynyl)borane

Trimethylsilylethyne is reacted with methylmagnesium chloride in tetrahydrofuran. The trimethylsilylethynylmagnesium chloride obtained is reacted with $BCl_3$. The $MgCl_2$ is filtered off and the solvent is removed in vacuo.

EXAMPLE 4

Preparation of Lithium tetrakis(triisopropylsilylethynyl)borate

Triisopropylsilylethyne is reacted with tert-butyllithium in toluene. The lithium triisopropylacetylide obtained is reacted with $BCl_3$ in tetrahydrofuran. The LiCl is filtered off and the solvent is removed in vacuo.

EXAMPLE 5

Preparation of lithium tetrakis(tritert-butylsilylethynyl)borate

Tert-butylsilylethyne is reacted with tert-butyllithium in toluene. The lithium tritert-butylacetylide obtained is reacted with $BF_3$ in tetrahydrofuran. The LiF is filtered off and the solvent is removed in vacuo.

EXAMPLE 6

Preparation of N,N-dimethylphenylammonium tetrakis(tert-butylsilylethynyl)borate Lithium tetrakis(tritert-butylsilylethynyl)borate is dissolved in toluene and one equivalent of N,N-dimethylphenylammonium chloride is added. The LiCl which has precipitated out is filtered off. After removal of the toluene in vacuo, N,N-dimethylphenylammonium tetrakis(tritert-butylsilylethynyl)borate is obtained.

EXAMPLE 7

Preparation of N,N-dimethylphenylammonium tetrakis(triisopropylsilylethynyl)borate Lithium tetrakis(triisopropylsilylethynyl)borate is dissolved in toluene and one equivalent of N,N-dimethylphenylammonium chloride is added. The LiCl which has precipitated out is filtered off. After removal of the toluene in vacuo, N,N-dimethylphenylammonium tetrakis(triisopropylsilylethynyl)borate is obtained.

EXAMPLE 8

Preparation of triphenylcarbonium tetrakis(triisopropylsilylethynyl)borate

Lithium tetrakis(triisopropylsilylethynyl)borate is dissolved in toluene and one equivalent of chlorotriphenylmethane is added. The LiCl that has precipitated out is filtered off. After removal of the toluene in vacuo, triphenylcarbonium tetrakis(triisopropylsilylethynyl)borate is obtained.

The invention claimed is:

1. A coordination compound selected from the group consisting of
lithium tetrakis(trimethylsilylethynyl)borate, lithium tetrakis(triisopropylsilylethynyl)borate, lithium tetrakis (tritertbutylsilylethynyl)borate, N,N-dimethylphenylammonium tetrakis(tritert-butylsilylethynyl)borate and N,N-dimethylphenylammonium tetrakis(triisopropylsilylethynyl)borate.

2. A galvanic cell comprising an electrolyte and the coordination compound of claim 1.

3. A lithium ion battery comprising lithium and the coordination compound of claim 1.

4. An electrolytic double-layer capacitor comprising a coordination compound according to claim 1.

5. A method for catalyzing or synthesizing a substance comprising, performing an organic synthesis with a coordination compound according to claim 1.

6. An electrolyte comprising the coordination compound according to claim 1.

7. A conductive salt comprising a coordination compound according to claim 1.

8. Lithium tetrakis(trimethylsilylethynyl)borate.

9. Lithium tetrakis(triisopropylsilylethynyl)borate.

10. Lithium tetrakis(tritertbutylsilylethynyl)borate.

11. N,N-dimethylphenylammonium tetrakis(tritert-butylsilylethynyl)borate.

12. N,N-dimethylphenylammonium tetrakis(triisopropylsilylethynyl)borate.

* * * * *